(12) United States Patent
Jung et al.

(10) Patent No.: US 11,278,515 B2
(45) Date of Patent: Mar. 22, 2022

(54) COMPOSITION FOR IMPROVEMENT OF SLEEP OR FOR PREVENTION OR TREATMENT OF SLEEP DISORDERS, CONTAINING BETA-LAPACHONE

(71) Applicants: AJOU UNIVERSITY INDUSTRY-ACADEMIC COOPERATION FOUNDATION, Suwon-si (KR); UNIVERSITY-INDUSTRY COOPERATION GROUP OF KYUNG HEE UNIVERSITY, Yongin-si (KR)

(72) Inventors: Yi-Sook Jung, Yongin-si (KR); Tae Ho Kim, Pyeongtaek-si (KR); Se Young Choung, Seoul (KR)

(73) Assignees: AJOU UNIVERSITY INDUSTRY-ACADEMIC COOPERATION FOUNDATION, Suwon-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 301 days.

(21) Appl. No.: 16/471,760

(22) PCT Filed: Dec. 19, 2017

(86) PCT No.: PCT/KR2017/015051
§ 371 (c)(1),
(2) Date: Nov. 18, 2019

(87) PCT Pub. No.: WO2018/117612
PCT Pub. Date: Jun. 28, 2018

(65) Prior Publication Data
US 2020/0113867 A1 Apr. 16, 2020

(30) Foreign Application Priority Data

Dec. 20, 2016 (KR) .................. 10-2016-0174553

(51) Int. Cl.
*A61K 31/352* (2006.01)
*A61P 25/20* (2006.01)

(52) U.S. Cl.
CPC ............ *A61K 31/352* (2013.01); *A61P 25/20* (2018.01)

(58) Field of Classification Search
CPC ............................. A61K 31/352; A61P 25/20
See application file for complete search history.

(56) References Cited

U.S. PATENT DOCUMENTS

2009/0292011 A1    11/2009    Yoo et al.

FOREIGN PATENT DOCUMENTS

| KR | 10-2014-0054527 A | 5/2014 |
|---|---|---|
| KR | 10-1501612 B1 | 3/2015 |
| KR | 10-2016-0081588 A | 7/2016 |
| WO | 2004/045557 A2 | 6/2004 |

OTHER PUBLICATIONS

Dagan et al. ("Sleep-wake schedule disorder disability: a lifelong untreatable pathology of the circadian time structure." Chronobiol Int. Nov. 2001;18(6):1019-27. doi: 10.1081/cbi-100107975. Abstract.) (Year: 2001).*
NINDS ("Hypersomnia Information Page _ National Institute of Neurological Disorders and Stroke." (Mar. 2019) https://www.ninds.nih.gov/Disorders/All-Disorders/Hypersomnia-Information-Page). (Year: 2019).*
International Search Report for PCT/KR2017/015051 dated Apr. 6, 2018 [PCT/ISA/210].

* cited by examiner

*Primary Examiner* — Jeffrey S Lundgren
*Assistant Examiner* — Chris E Simmons
(74) *Attorney, Agent, or Firm* — Sughrue Mion, PLLC

(57) ABSTRACT

The present invention relates to a pharmaceutical composition or a health functional food composition for improving sleep or preventing or treating sleep disorders comprising beta-lapachone as an active ingredient. Beta-lapachone decreases the sleep latency and increases the total sleeping time, and thus the composition comprising the beta-lapachone can effectively improve sleep and prevent and treat sleep disorders.

3 Claims, 2 Drawing Sheets

[FIG. 1]
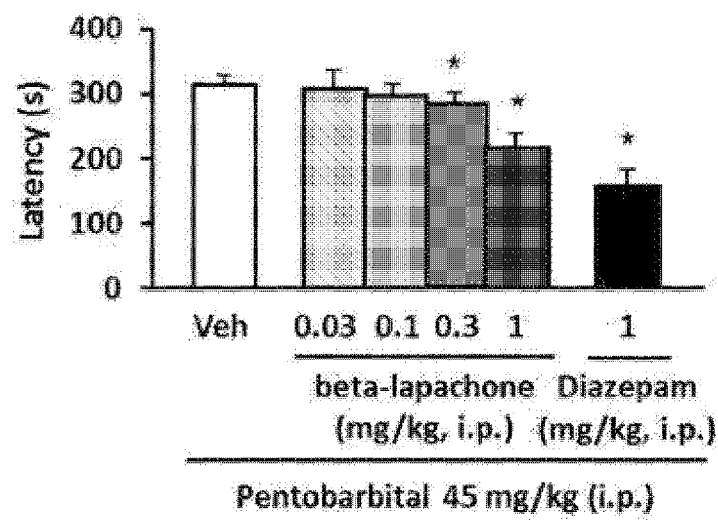
[FIG. 2]
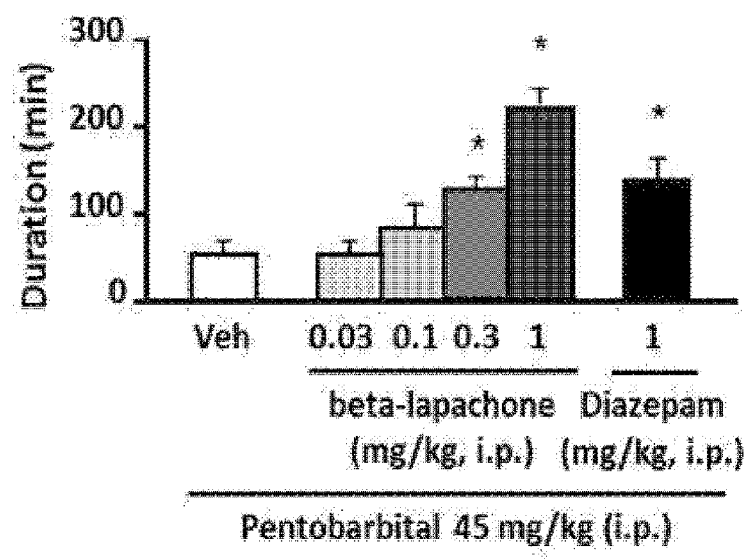

[FIG. 3]
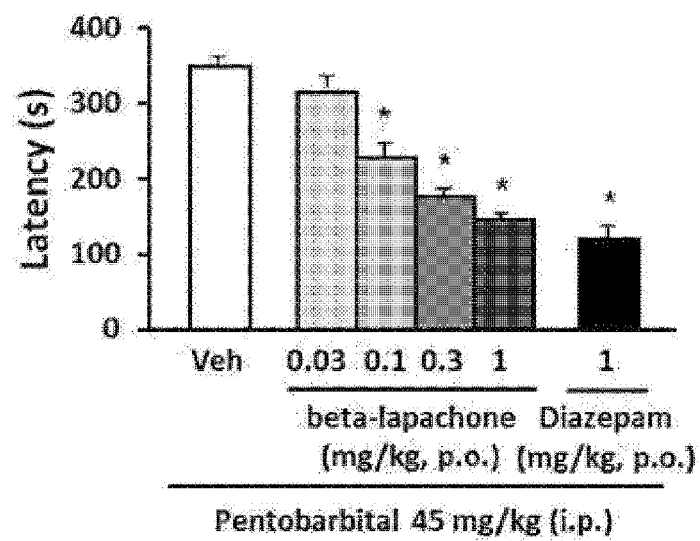
[FIG. 4]
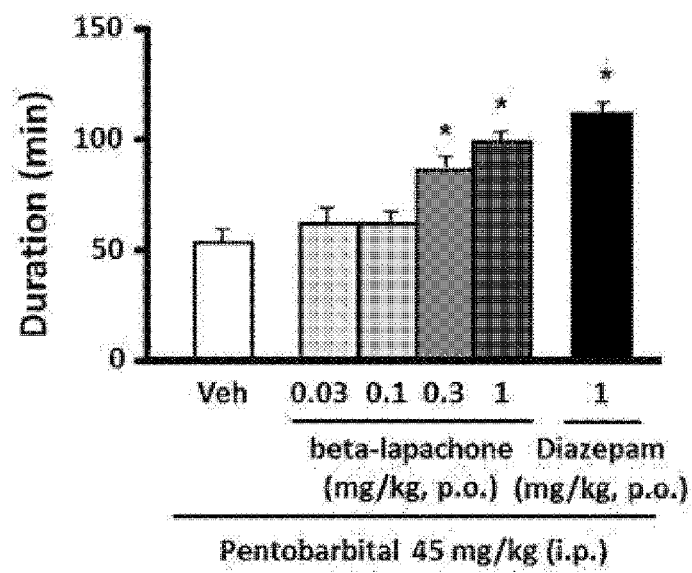

COMPOSITION FOR IMPROVEMENT OF SLEEP OR FOR PREVENTION OR TREATMENT OF SLEEP DISORDERS, CONTAINING BETA-LAPACHONE

CROSS-REFERENCE TO RELATED APPLICATIONS

This application is a National Stage of International Application No. PCT/KR2017/015051 filed Dec. 19, 2017, claiming priority based on Korean Patent Application No. 10-2016-0174553 filed Dec. 20, 2016.

TECHNICAL FIELD

The present invention relates to a pharmaceutical composition or a health functional food composition for improving sleep or for preventing or treating sleep disorders comprising a beta-lapachone.

BACKGROUND ART

Sleep refers to the state in which the conscious activity is relaxed with eyes closed and it is an important process to recover the fatigue accumulated by physical activity and to supplement the energy used by people during daytime activities. Sleep is not only the time to restore energy and fatigue but also the time when the growth hormone which is essential for human growth is most secreted. The brain in our body is responsible for all the physiological functions for maintaining life, and rest is necessary to maintain a balance of appropriate activities. Most of these rest is done during sleeping time.

However, the number of patients diagnosed and treated for sleep problems due to the exhausting and busy routine of modern life and the aging of the population have increased in recent years and are expected to increase steadily in the future. According to the National Sleep Foundation, a survey in 2005, ten of the active population is reported that they were absent or made mistakes in their work due to sleep-related problems.

Disorders associated with sleep are directly harmful to the health and recent studies have shown that lack of sleep increases the risk for diabetes, heart disease, and obesity. In the study of Journal 'Sleep' published in 2004, women who sleep less than five hours at night on average had significantly higher mortality rates than women who sleep for seven hours.

Currently, the administration of sleeping pills, tranquilizers, and stress relievers, to treat insomnia or sleep disorder has been used as a common treatment. However, a long-term dose of these drugs for at least 4 weeks occurs problems of dependency and drug side effects, and in the case of elderly or pregnant women the administration of such drugs may be limited. Accordingly, there is a need to develop a medicament made of a natural substance capable of effectively improving or treating sleep disorders with fewer side effects besides the above-mentioned drugs.

Meanwhile, beta-lapachone is a natural quinone substance obtained from lapacho tree (*Tabebuia avellanedae*), which can also be extracted from various plants. Studies to date have shown that beta-lapachone has anticancer, anti-inflammatory, and antifungal effects, but there has been no report on the effects of treating or improving sleep or sleep disorders.

DISCLOSURE

Technical Problem

It is an objective of the present invention to provide a pharmaceutical composition capable of improving sleep or effectively preventing or treating sleep disorders.

It is another objective of the present invention to provide a health functional food composition capable of improving sleep or effectively preventing or improving sleep disorders.

Technical Solution

In order to achieve the above objectives, the present invention provides a pharmaceutical composition for preventing or treating sleep disorders comprising beta-lapachone or a pharmaceutically acceptable salt thereof as an active ingredient.

Also, the present invention provides a pharmaceutical composition for improving sleep comprising beta-lapachone or a pharmaceutically acceptable salt thereof as an active ingredient.

To achieve another objective, the present invention provides a health functional food composition for preventing or improving sleep disorder comprising beta-lapachone or a pharmaceutically acceptable salt thereof as an active ingredient.

In addition, the present invention provides a health functional food composition for improving sleep comprising beta-lapachone or a pharmaceutically acceptable salt thereof as an active ingredient.

Advantageous Effects

According to the present invention, beta-lapachone has the effect of improving sleep by decreasing the sleep latency and increase the total sleeping time, and the composition comprising the same as an active ingredient contains a natural product as an effective ingredient and it can effectively improve sleep and prevent and treat sleep disorders while having fewer side effects.

DESCRIPTION OF DRAWINGS

FIG. 1 shows a result of confirming the effect of shortening the sleep latency when the beta-lapachone is administered to mice by intraperitoneal injection in an embodiment of the present invention.

FIG. 2 shows a result of confirming the increase in total sleeping time when the beta-lapachone is administered to mice by intraperitoneal injection in the embodiment of FIG. 1.

FIG. 3 shows a result of confirming the effect of shortening the sleep latency when the beta-lapachone is administered to mice by oral administration in the embodiment of FIG. 1.

FIG. 4 shows a result of confirming the increase in total sleeping time when the beta-lapachone is administered to mice by oral administration in the embodiment of FIG. 1.

BEST MODE

The inventors of the present invention have investigated a method of improving sleep or effectively preventing or treating sleep disorders and found that sleeping in mice treated with beta-lapachone remarkably improved and completed the present invention.

Accordingly, the present invention provides a pharmaceutical composition for preventing or treating sleep disorders comprising beta-lapachone or a pharmaceutically acceptable salt thereof as an active ingredient.

The present invention also provides a pharmaceutical composition for improving sleep comprising of beta-lapachone or a pharmaceutically acceptable salt thereof as an active ingredient.

In the present invention, the "beta-lapachone" is a natural substance that can be extracted from the bark of Lapacho which is mainly found in South America and is metabolized by an enzyme called NADP(H) dehydrogenase (quinone, NQO1) which is synthetized much in solid cancer cells, thereby having an effect of damaging or necrosing the cancer cells and thus it have been researched as a natural anticancer agents and is also attracting the attention as a medicinal agent that can prolong the life span by inhibiting aging.

The beta-lapachone can reduce the sleep latency or increase the total sleeping time in a concentration-dependent manner, so that the pharmaceutical composition comprising beta-lapachone can improve sleep or effectively prevent or treat sleep disorder.

At this time, the sleep disorder may be at least one selected from the groups consisting of insomnia, narcolepsy, abnormal behavior during sleep and hypersomnia, but it is not limited thereto if it is sleep related disease.

In the present invention, the term "insomnia" is the primary symptom of sleep disorder and it includes a sleeping disorder that is having a difficulty of falling asleep even if when one is already in bed, a sleep maintenance disorder in which the number of times one wakes up overnight is five times or more, and an early arousal disorder that one wakes up early and cannot fall asleep again.

In the present invention, the term "narcolepsy" is a neurologic disorder that involves a dysfunction for sleep-wake cycles. Symptoms include excessive daytime sleepiness (the main symptom), cataplexy (episodic loss of muscle function triggered by sudden emotional stimulus such as laughter, anger, or fear), sleep paralysis (temporary inability to talk or move when waking or falling asleep), and hypnagogic hallucination (vivid, often frightening, dreamlike experiences that occur while dozing or falling asleep.

In the present invention, the term "abnormal behavior during sleep" is a symptom in which a motion or behavior that does not occur during normal sleep, such as restless leg syndrome, sleep paralysis, nightmare, REM sleep disorder, sleepwalking, and night terrors. The restless legs syndrome is a syndrome that one feels the urge to move one's legs because one feels an unpleasant sensation such as creepiness or numbness in the legs and sometimes one cannot stand the urge and has to shake or twist the legs while sleeping.

In the present invention, the term "hypersomnia" refers to a state of sleep disorder in which one gets drowsy in daytime and is hindered from daily tasks even though with a sufficient sleep time because one has not taken a deep sleep at night, regardless of the abnormal expression of REM sleep. Unlike narcolepsy, there is no 'sleeping seizure' symptom that one cannot notice when one suddenly falls asleep.

Meanwhile, the beta-lapachone may be contained in an amount of 0.01 to 200 parts by weight based on 100 parts by weight of the pharmaceutical composition. When it is contained in an amount of less than 0.01 part by weight, the effect of improving the sleep disorder of the beta-lapachone cannot be exhibited and when it is contained in an amount of more than 200 parts by weight, is not preferable since the increase in effect according to the amount of beta-lapachone is insignificant and the stability of the formulation becomes unstable.

The term "prevention" as used herein refers to any action that inhibits or delays sleep disorder by the administration of a composition comprising the beta-lapachone or a pharmaceutically acceptable salt thereof. The term "treatment" as used herein refers to any action in which the symptom of sleep disorder is improved or cured by the administration of a composition comprising the beta-lapachone or a pharmaceutically acceptable salt thereof.

The beta-lapachone of the present invention can be used in the form of a pharmaceutically acceptable salt and such salts include acid addition salts formed by pharmaceutically acceptable free acids or metal salts formed by the base. An inorganic acid and an organic acid may be used as the free acid, as an inorganic acid, hydrochloric acid, sulfuric acid, bromic acid, sulfurous acid, phosphoric acid or the like may be used. The metal salts include alkali metal salts or alkaline earth metal salts, and sodium, potassium or calcium salts are useful.

The composition of the present invention may contain, for administration, a pharmaceutically acceptable carrier, excipient or diluent in addition to the above-described active ingredient. Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate and mineral oil.

The pharmaceutical compositions of the present invention may be formulated in the form of oral preparations such as powders, granules, tablets, capsules, suspensions, emulsions, syrups, aerosols and the like, external applications, suppositories and sterilized injection solutions according to a conventional method. Specifically, in the case of formulation, a diluent or excipient such as commonly used filler, an extender, a binder, a wetting agent, a disintegrant, a surfactant or the like is used. Solid formulations for oral administration include tablets, pills, powders, granules, capsules, etc., but they are not limited thereto. Such solid formulations may contain at least one excipient such as starch, calcium carbonate, sucrose, lactose, gelatin and the like in addition to the beta-lapachone or a pharmaceutically acceptable salt thereof. Furthermore, in addition to simple excipients, lubricants such as magnesium stearate and talc are also used. Examples of the liquid formulations for oral administration include various excipients such as wetting agents, sweeteners, fragrances and preservatives and the like in addition to liquid paraffin. Formulations for parenteral administration include sterile aqueous solutions, non-aqueous solutions, suspensions, emulsions, freeze-dried preparations, and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

A suitable dose of the composition of the present invention varies depending on the condition and weight of the patient, the degree of disease, the type of drug, and time, but can be appropriately selected by the person skilled in the art, and the daily dose of the beta-lapachone or a pharmaceutically acceptable salt thereof is preferably 0.01 mg/kg to 500 mg/kg, and may be administered once to several times a day, if necessary.

Furthermore, the present invention provides a health functional food composition for preventing or improving sleep disorder comprising beta-lapachone or a pharmaceutically acceptable salt thereof as an active ingredient.

The present invention also provides a health functional food composition for improving sleep comprising beta-lapachone or a pharmaceutically acceptable salt thereof as an active ingredient.

The beta-lapachone can reduce the sleep latency or increase the total sleeping time in a concentration-dependent manner, so that the health functional food composition comprising beta-lapachone can improve the sleep or effectively prevent or improve sleep disorders.

At this time, the sleep disorder may be at least one selected from the groups consisting of insomnia, narcolepsy, abnormal behavior during sleep and hypersomnia, but it is not limited thereto if it is sleep related disease.

The health functional food composition may contain various nutrients, vitamins, minerals (electrolytes), flavors such as synthetic flavors and natural flavors, etc., colorants and fillers (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated drinks, and the like. It may also contain flesh for the production of natural fruit juices, synthetic fruit juices and vegetable drinks. These components may be used independently or in combination. In addition, the health functional food composition may be in the form of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive, and its suitability as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned "Korean Food Additives Codex" include chemical synthetics such as ketones, glycine, potassium citrate, nicotinic acid, and cinnamic acid and the like, natural additives such as persimmon extract, licorice extract, crystalline cellulose, kaoliang color and guar gum and the like, mixed preparations such as L-sodiumglutamate preparation, alkaline agents for noodles, preservative formulation and a tar color formulation and the like.

At this time, the content of the beta-lapachone or a pharmaceutically acceptable salt thereof according to the present invention added to the food during the production of the health functional food composition can be appropriately increased or decreased as needed.

Hereinafter, the present invention will be described in detail with reference to the following examples. It should be noted, however, that the following examples are provided to more fully describe the present invention to those skilled in the art and are illustrative of the present invention and are not intended to limit the scope of the present invention.

Example 1

A sleep disorder refers to syndromes in which one cannot fall asleep well and the total sleeping time is short. In order to confirm the effect of improving the sleep quality of beta-lapachone, mice were purchased from Orient Bio Co. Beta-lapachone (Sigma Aldrich) was administered once intraperitoneally or orally to mice at a dose of 0.03, 0.1, 0.3, or 1 mg/kg by concentration, respectively, 30 minutes before induction of sleep, and 0.9% physiological saline was administered to the control mice, and 1 mg/kg of diazepam (MYUNG IN Pharm. Co.), most popular used sleeping pill, was administered intraperitoneally or orally to the positive control mice. 45 mg/kg of pentobarbital (HANLIM Pharm. Co., Ltd.), a commercially used sedative and sleeping pill, was intraperitoneally administered to mice to induce sleeping after 30 minutes of the above administration.

Then, the sleep latency and the total sleeping time are measured and are shown in FIGS. 1, 2, 3 and 4. As a result, referring to FIG. 1 (group of intraperitoneal administration) and FIG. 3 (group of oral administration), the sleep latency was about 300 seconds for the control group which was treated with 0.9% physiological saline, however in the case of mice to which beta-lapachone was administered once orally or intraperitoneally, the sleep latency was shortened in a concentration-dependent manner.

In addition, referring to FIG. 2 (group of intraperitoneal administration) and FIG. 4 (group of oral administration), the total sleeping time was increased in a concentration-dependent manner in mice to which beta-lapachone was administered intraperitoneally or orally once, and especially, when beta-lapachone was administered at a dose of 0.3 mg/kg or more, it showed similar or better effects to the diazepam-induced effects in the positive control group.

Therefore, the composition of the present invention comprising beta-lapachone can effectively improve the sleeping quality and furthermore, there is a possibility of treating sleep disorders.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method for preventing, improving or treating insomnia comprising administering a composition comprising beta-lapachone or a pharmaceutically acceptable salt thereof as an active ingredient to a subject in need thereof.

2. The method according to claim 1, wherein the beta-lapachone reduces sleep latency or increases total sleeping time in a concentration-dependent manner.

3. The method according to claim 1, wherein the beta-lapachone is in an amount of 0.01 to 100 parts by weight based on 100 parts by weight of the composition.

* * * * *